(12) United States Patent
Heaton

(10) Patent No.: US 6,730,115 B1
(45) Date of Patent: May 4, 2004

(54) COOLING SYSTEM

(75) Inventor: Keith Patrick Heaton, Dorset (GB)

(73) Assignee: KCI Licensing, Inc., San Antonio, TX (US)

(*) Notice: Subject to any disclaimer, the term of this patent is extended or adjusted under 35 U.S.C. 154(b) by 0 days.

(21) Appl. No.: 09/193,071

(22) Filed: Nov. 16, 1998

Related U.S. Application Data

(63) Continuation of application No. PCT/GB97/01344, filed on May 16, 1997.

(30) Foreign Application Priority Data

May 16, 1996 (GB) .............................................. 9610233

(51) Int. Cl.[7] .................................................. A61F 7/12
(52) U.S. Cl. ........................... 607/104; 607/108; 5/421; 5/423; 5/706; 5/941
(58) Field of Search .................... 607/96, 104, 107, 607/108, 112; 5/421, 423, 482, 941, 706, 710

(56) References Cited

U.S. PATENT DOCUMENTS

| | | | | |
|---|---|---|---|---|
| 3,610,323 A | * | 10/1971 | Troyer ........................... | 165/46 |
| 4,170,998 A | | 10/1979 | Sauder ......................... | 128/400 |
| 4,423,308 A | | 12/1983 | Callaway et al. ............ | 219/217 |
| 4,572,188 A | | 2/1986 | Augustine et al. .......... | 128/380 |
| 4,638,519 A | | 1/1987 | Hess ............................. | 5/455 |
| 4,660,388 A | | 4/1987 | Greene, Jr. ................... | 62/261 |
| 4,777,802 A | | 10/1988 | Feher ............................. | 62/3 |
| 4,867,230 A | | 9/1989 | Voss .............................. | 165/46 |
| 4,907,308 A | | 3/1990 | Leininger et al. ............ | 5/455 |
| 4,966,145 A | | 10/1990 | Kikumoto et al. .......... | 128/377 |
| 5,081,339 A | | 1/1992 | Stine ............................. | 219/217 |
| 5,097,548 A | | 3/1992 | Heck et al. .................... | 5/414 |
| 5,125,238 A | | 6/1992 | Ragan et al. ............... | 62/259.3 |
| 5,165,127 A | | 11/1992 | Nicholson ...................... | 5/421 |
| 5,168,589 A | * | 12/1992 | Stroh et al. .................... | 5/710 |
| 5,300,098 A | * | 4/1994 | Philipot ........................ | 607/96 |
| 5,350,417 A | | 9/1994 | Augustine ................... | 607/104 |
| 5,392,847 A | | 2/1995 | Stephenson .................. | 165/46 |
| 5,473,783 A | | 12/1995 | Allen ............................. | 5/469 |
| 5,655,237 A | * | 8/1997 | Suzuki et al. .................. | 5/502 |

FOREIGN PATENT DOCUMENTS

| | | | |
|---|---|---|---|
| EP | 0 113 420 A1 | 11/1983 | ............. A61F/5/00 |
| GB | 783350 | 9/1957 | |
| GB | 2 263 872 A | 11/1993 | ............. A61F/7/00 |
| WO | WO 95/10211 | 4/1995 | ........... A47C/27/08 |
| WO | WO 97/14380 | 4/1997 | ............. A61F/7/00 |

OTHER PUBLICATIONS

British Search Report; British patent application GB 9710138.0 (continuation of GB 9610233.0); Aug. 20, Oct. 28, 1997.

PCT International Search Report; PCT international application PCT/GB97/01344; Oct. 23, 1997.

PCT International Preliminary Examination Report; PCT international application PCT/GB97/01344; Aug. 24, 1998.

* cited by examiner

*Primary Examiner*—Rosiland K. Rollins

(57) ABSTRACT

A cooling system for cooling a person in a supine position as part of a clinical treatment includes an air blower, a heat exchanger, an inflatable mattress and a cooling jacket or overlay. Air from the blower is cooled by contact with the heat exchanger, passed through the jacket or overlay and through the mattress in order to rapidly cool the person so as to achieve mild hypothermia.

23 Claims, 4 Drawing Sheets

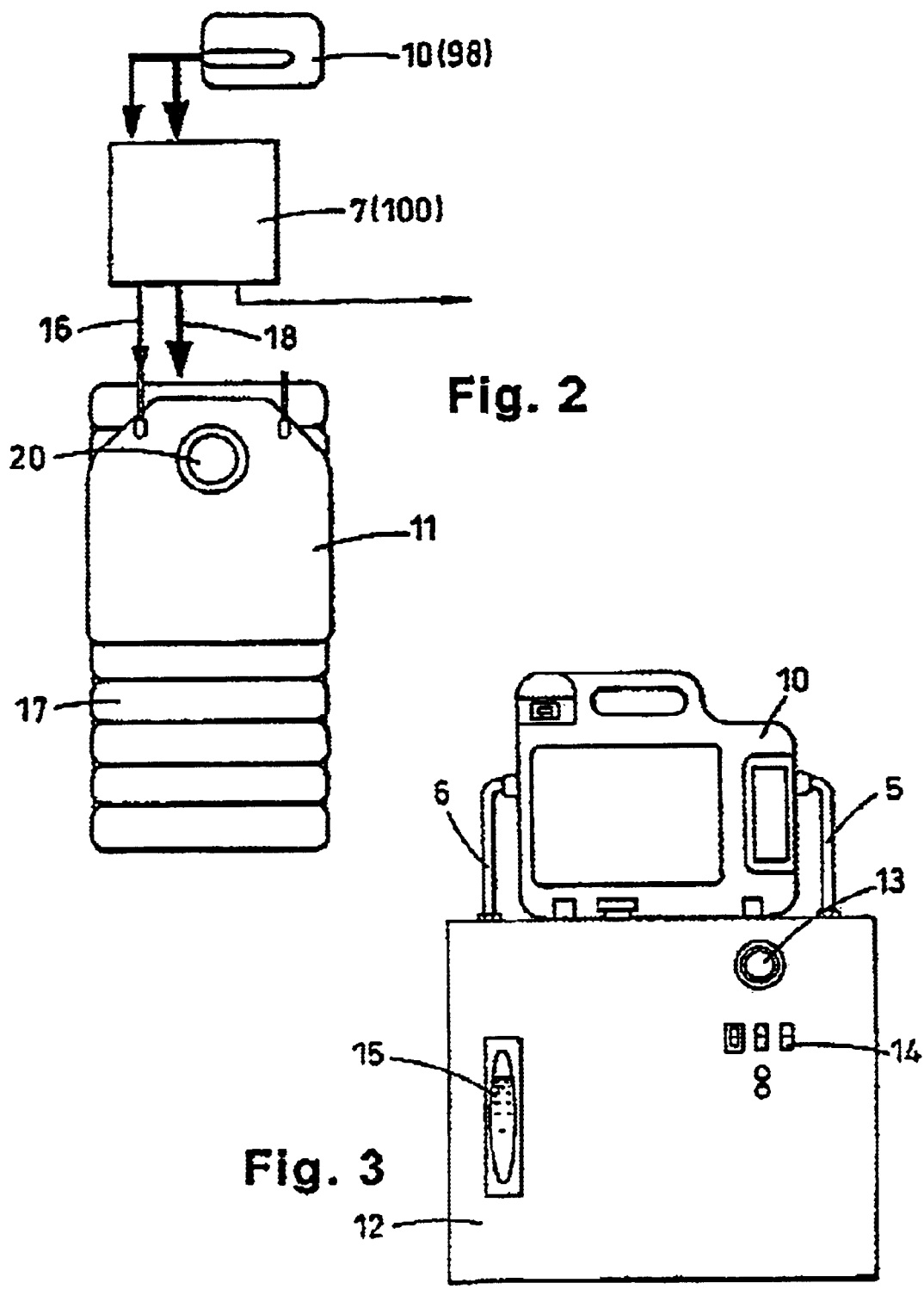

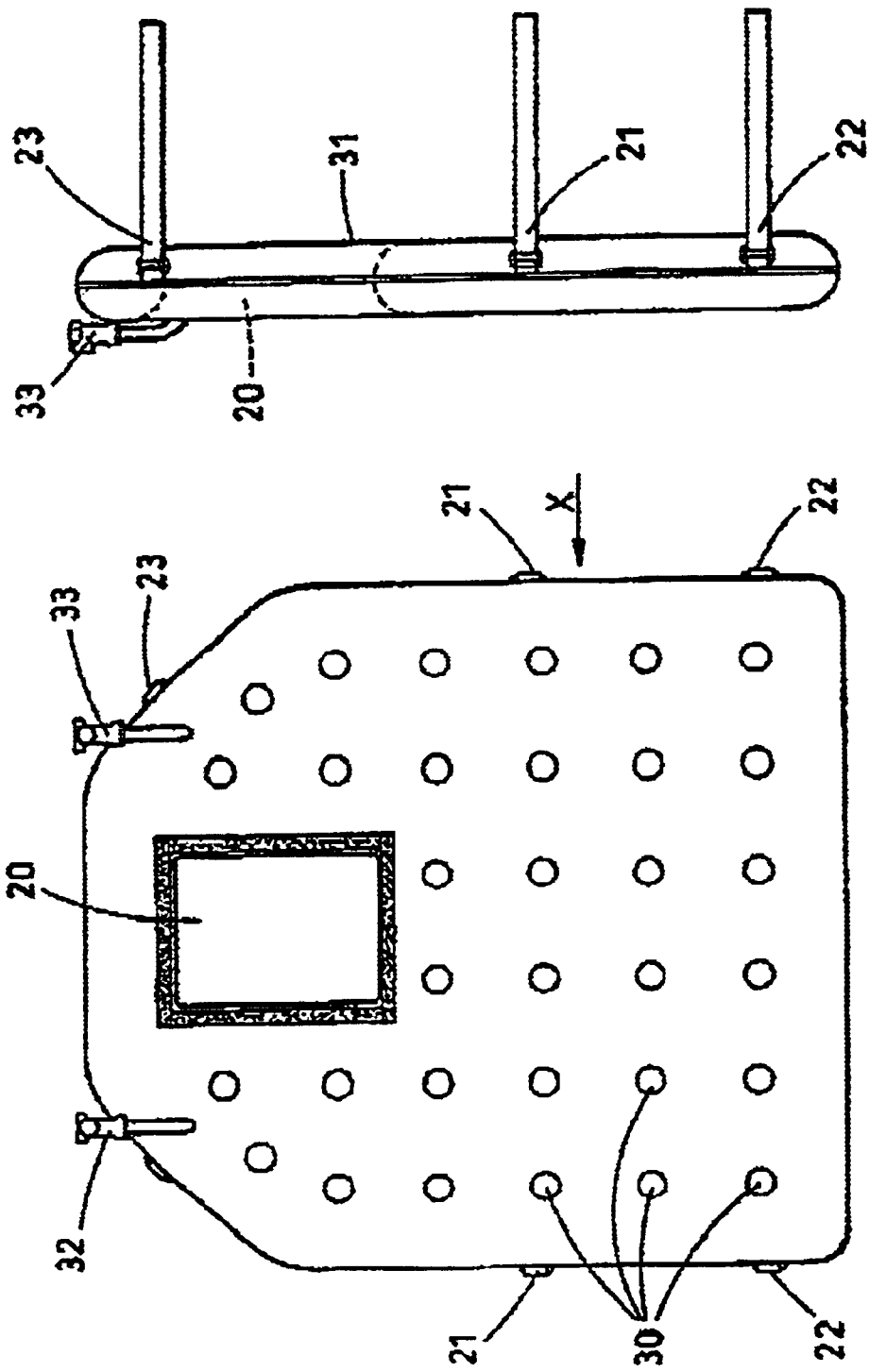

COOLING SYSTEM

RELATED APPLICATIONS

This application is a continuation, under 35 U.S.C. §120, of co-pending international application (designating the United States) Ser. No. PCT/GB97/01344 filed May 16, 1997 and claims foreign priority, under 35 U.S.C. §119, to British patent application Ser. No. 9610233.0 filed May 16, 1996. By this reference, the full disclosure of international application Ser. No. PCT/GB97/01344 is incorporated herein as though now set forth in its entirety.

FIELD OF THE INVENTION

The present invention relates to cooling systems. More particularly, the invention relates to cooling systems for cooling a person in a supine position.

BACKGROUND OF THE INVENTION

There are circumstances in which it may be desirable to positively cool a patient as part of clinical treatment. For example, recent investigations have indicated that benefits may arise by subjecting patients who have suffered a stroke or cardiac arrest to mild hypothermia, e.g. a temperature in the range of 32 to 34° C. for a period of more than about 1 hour after the cardiac arrest. This clinical procedure is described in the paper by Fritz Sterz et al. in the Journal of Neurological Anaestheology, Volume 8, No. 1, pages 88 to 96, published 1996.

It is, therefore, an object of the present invention to provide a method and equipment for carrying out such a clinical procedure, as well as for cooling patients for other purposes.

SUMMARY OF THE INVENTION

According to one aspect of the present invention, therefore, there is provided a method of cooling a person in a supine position on a support which comprises passing cooled air through a flexible jacket which underlies or overlays the person, said jacket preferably having apertures to allow escape of cooling air. Preferably, the jacket is adapted to overlay the person and to cover at least his torso. In an especially preferred form, the jacket or blanket substantially covers the person from head to foot.

The present invention includes a mattress which is associated with a heat exchanger, the heat exchanger being connectable to a source of cooling fluid such as water so that the patient may be cooled as required, by connecting the heat exchanger to a source of cooled liquid, such as refrigerant.

According to a further feature of the present invention, therefore, there is provided a mattress having inflatable compartments for supporting a person thereon, and an air supply means for supplying pressurized air to the mattress, said mattress having a heat exchanger associated therewith, through which said pressurized air can be passed and said heat exchanger being connectable as required to a source of cooling fluid, such as a refrigeration circuit, whereby pressurized air can be cooled as required, and applied directly to the patient or to a jacket or blanket in contact with the patient.

Preferably, in such a mattress, the source of air comprises a pump unit having an outlet for connection to the inflatable compartments, and an outlet for connection to an inflatable cooling jacket or blanket.

The heat exchanger may be located in a housing physically attached to the mattress or to a bed on which the mattress is supported. Alternatively, the heat exchanger may be contained in a separate unit and connected to the mattress (and/or cooling jacket or blanket) by conduits, which are normally flexible.

The heat exchanger is conveniently supplied with cooling liquid, either by being incorporated in a refrigeration circuit in which the heat exchanger is on the expansion side, or fed with cooling fluid from a refrigeration system. In the latter case, the cooling fluid s generally water or an aqueous liquid such as brine, and is cooled by contact with the heat exchanger of a refrigeration circuit. This arrangement has the advantage that the cooling fluid circuit, such as water, provides a heat reservoir which irons out sharp fluctuations in temperature in the system. However, the former, more direct, cooling system works satisfactorily and has a quicker start up and will attain steady state more quickly. Preferably, a regulator valve is introduced into the refrigeration circuit and controls the flow of refrigerant as required to maintain a desired temperature at the supporting surface of the mattress. This can be achieved, for example, by using a solenoid regulator hot gas by-pass valve in the refrigeration circuit, which is controlled by a digital PID controller connected to one or more temperature sensors at the exit end of the heat exchanger.

It is convenient to extract heat from an air stream by blowing air over the heat exchanger and feeding the pressurized, cold air to the mattress and also to the cooling jacket or blanket. Normally, the air supplied to the mattress is intended to be sufficient to provide support for the patient as well as to provide the desired cooling effect. Where the same blower is used to supply air both to the mattress and jacket/blanket, the majority of the air will be directed to the mattress.

Some of the air supplied to the mattress will pass to atmosphere via exhaust valves in the mattress for controlling air pressures in the inflated compartments of sacs of the mattress. Other quantities of air will escape via stitch holes in the surface of the mattress and form air streams which cool the patient by passing over his skin. Heat will also be abstracted from the patient by conduction through the surface of the mattress and by cooling air emitted from apertures in the cooling jacket or blanket.

It may be necessary to provide means to confine the patient to prevent shivering.

In the operation of the patient cooling system of the invention, the objective is to effect moderate to mild hypothermia, i.e. a body temperature of about 32 to 34° C. It is found that this can be achieved with the mattress and jacket/blanket of this invention using an air input temperature to the apparatus of about 1 to 3° C., preferably about 2° C. The mattress surface temperature should be less than 10° C., preferably about 5 to 10° C. Studies have indicated that clinical benefits are obtained in terms of reduction in brain damage if the temperature of the patient who has suffered cardiac arrest is reduced to a temperature in the range of 32 to 34° C. within a few hours, preferably within 2 to 4 hours, of restoration of spontaneous circulation (ROSC). Hypothermia treatment needs to be started quickly after ROSC, e.g. within about 15 minutes.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed descrip

FIG. 2 is a schematic representation of the application of the system of FIG. 1 or 1A to a cooling jacket;

FIG. 3 is a view in elevation showing the cooling and blower pump unit;

FIG. 4 is a plan view of a cooling jacket of the kind shown in FIG. 2;

FIG. 5 is a view of the jacket shown in FIG. 4 in the direction of the arrow X in FIG. 4.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 1:
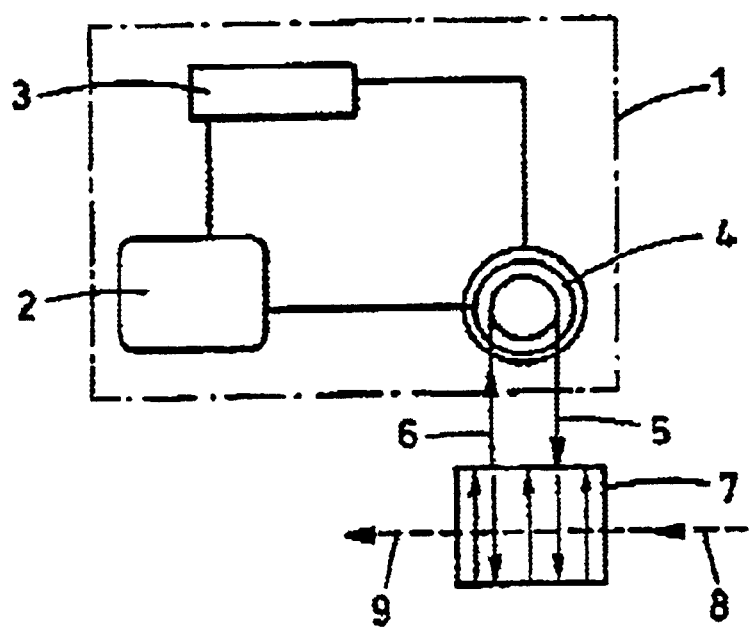
- FIG. 1 is a schematic illustration of a patient cooling system in accordance with the invention.

Referring to the accompanying drawings, and in particular to FIG. 1, in one form, the cooling system essentially comprises a refrigeration unit 1, comprising a compressor 2, a condenser 3 and an evaporation coil 4, through which the refrigerant is circulated. Water is circulated through the evaporation coil and the cooled water is circulated through pipes 5 and 6, to a heat exchanger 7. Air is passed through the heat exchanger 7 from a pump (not shown) as indicated schematically by the arrow 8 and the cooled air is then passed as indicated by the arrow 9 to the mattress.

Figure 1A:
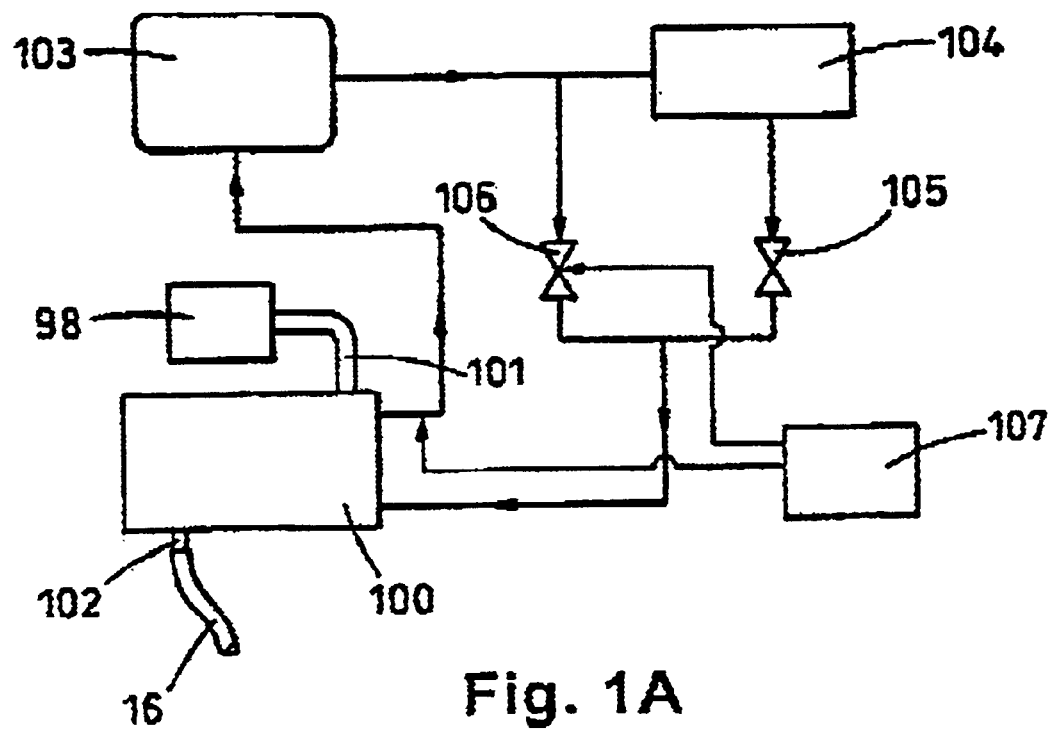
FIG. 1A is a schematic illustration of an alternative system.

Referring to FIG. 1A, this shows an alternative system for providing a stream of controlled cooling air. A heat exchanger 100 has an inlet 101 for air from a blower 98 and an outlet 102 for a stream of cooled air which is connected to a flexible conduit 16, for connection to a mattress and cooling jacket, e.g. as show in FIG. 2. Heat exchanger 100 is connected directly to a refrigeration circuit which includes a compressor 103 and a condenser 104 and an expansion valve 105 and a by-pass valve 106. The by-pass valve is controlled by control means 107 which is linked to a thermistor which is connected to the refrigerant circuit at the exit from the heat exchanger, such that, e.g. a fall in temperature at the heat exchanger exit will signal the by-pass valve to open, reducing the system cooling capacity. The valve 106 which is preferably a solenoid valve, may be signaled to cycle on and off in response to temperature sensed at the heat exchanger outlet 102. Where the mattress is of the low air loss type and individual air supply conduits are connected to different sections of the bed, e.g. the head, torso, seat and foot sections, in order to maintain air pressures appropriate for each part of the body, it may be desired to control the volume of air flowing through each section. Adjustment and control of the rate of air flow on the sections may be used to maintain each section at a desired target temperature.

Figure 3A:
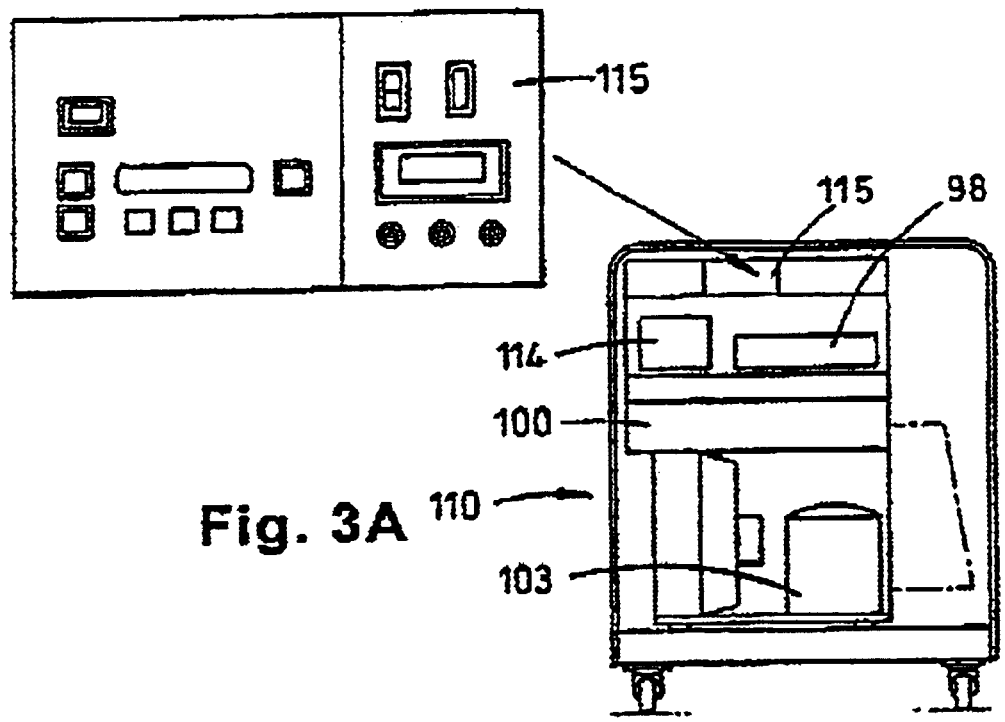
FIG. 3A illustrates a unit for housing a cooling system of the kind shown in FIG. 1A with a blower pump unit.

A cooling system of the kind shown in FIG. 1A may be housed in a blower/cooling unit as shown in FIG. 3A. This shows a unit 110 in which the refrigeration unit comprises a compressor 103 and heat exchanger 100 are housed in the lower part and a blower 98 and air valves 114 for controlling the flow of cooled air to the mattress and blanket/jacket are located. Thermocouples may be provided at various positions on the mattress, e.g. spaced at intervals from the head to the foot and connected to the blower 98 or the air valves 114. A control panel 115 is mounted on the front of the unit 110 and includes the controls and instruments indicated. The refrigeration and blower are thus combined in a single unit and flexible hoses (not shown) connect the unit to the mattress and blanket. The control panel may report temperatures recorded at the mattress support surface and may include an indication of the patient's core temperature.

The air system is shown in FIG. 2, which illustrates the connection of the pump unit 10 or 98 with the heat exchanger 7 or 100 and then to a cooling jacket 11. The pump unit comprises an air pump or compressor incorporating means for passing pressurized air through a tube, into the heat exchanger. The air pump 10 may include pressure regulating controls, including means for circulating a pulsating pressure flow to the heat exchanger. The heat exchanger and air cooling unit may include a thermostat 13, low temperature warning light 14 and water indicator level 15, indicating the amount of water in the reservoir. The use of a water reservoir irons out fluctuations in the temperature of the cooling air stream.

After passing through the heat exchanger, the air stream flows into the cooling jacket 11 via the line 16. The cooling jacket may include flow and return pipes 32 and 33 (FIGS. 4 and 5) and/or include apertures (not shown) in the cooling jacket which is preferably directed onto the patient's skin in order to effect cooling by convection and conduction.

Figure 6:
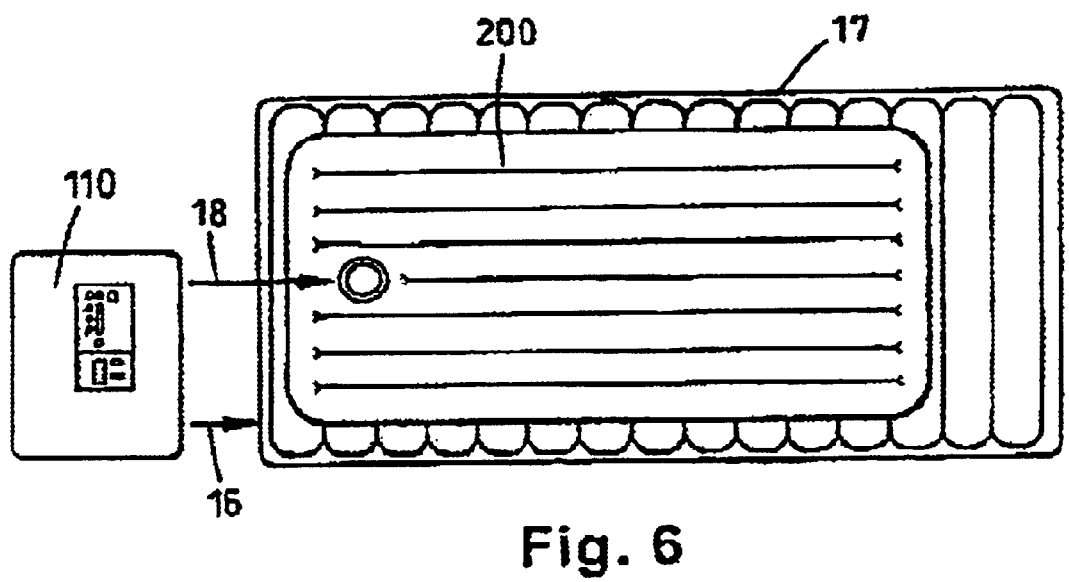
FIG. 6 shows a modified cooling system in accordance with the invention.

FIG. 6 shows a modified system comprising a cooling unit 110 (e.g. such as shown in FIG. 3A), connected to an inflatable low air loss mattress 17 and an inflatable overblanket 200. Separate flexible conduits 16 and 18 are provided to supply cooled air from the cooling unit to the mattress and overblanket, respectively. As shown in FIG. 6, the cooled air is supplied to the foot end of the overblanket 200. It will be appreciated that the supply 16 to the mattress may consist of separate conduits to different groups of air sacs in the mattress, each conduit supplying air at a pressure appropriate for the respective part of the patient's body.

As shown in FIGS. 2 and 6, the cooling jacket 11 or overblanket 200 is preferably placed on top of a mattress 17 which may be of the inflatable type. Preferred mattresses are those of the so-called low-air-loss type, in which air is circulated through the mattress and the surface of the individual sacs or compartments are provided with a moisture vapor permeable material, so that moisture produced by the patient flows into the sacs and is carried away in the air stream. Inflatable mattress supports of this kind are described in U.S. Pat. No. 4,525,885, EP document 0 034 954 and EP document 0 260 087. The mattress may alternatively be designed to provide pulsation therapy to the patient by cyclically varying pressures to the mattress, e.g. as described in U.S. Pat. No. 5,396,671.

In order to increase the rate of conduction of heat from the patient, the cooled air from the heat exchanger 7 or 100 may also be fed into the cushions of the mattress, thereby cooling the patient from below as well as above. The pump unit 10 or 98 may be provided with additional air outlets which by-pass the cooling unit if cooling from below is not required. Also, the pump unit may include pressure regulating features so that the individual cushions or groups of cushions in the mattress can be pressurized to a desired pressure, so as provide support for the patient over the maximum skin area.

FIGS. 4 and 5 show the construction of the cooling jacket in more detail. As can be seen from FIGS. 2 and 4, the jacket extends across the width of the mattress, and has an area that is designed to cover the torso, upper arms and head of the patient. The patient's nose and mouth is accessible through the aperture 20 so that a ventilation tube and other intensive care devices can be applied to the patient though this aperture.

The extreme edges of the jacket are provided with buckles and straps 21, 22 and 23, which can be passed around the mattress and the patient so as to hold the jacket in close contact with him.

The jacket comprises upper and lower layers of material which are air-impermeable, the two layers being welded at their edges so that the jacket forms an inflatable pad. Preferably, the upper and lower layers are welded together at intervals as shown at 30 so as to create a quilted effect.

Although not shown in the drawing, the lower layer 31 may be formed with a number of small, e.g. pinhole-like apertures through which inflation air may escape so as to produce a stream of cooling air flowing over the patient's body.

One type of cooling jacket which can be employed for the purposes of the invention comprises a disposable paper jacket. This can be manufactured from the kind of paper used to make paper towels or operating theatre gowns and hats. The jacket will be formed with an inner and outer layer and include punched holes to permit the cooling air to escape. Because the paper jacket is light, a large air flow is achieved at low inflation pressure.

In another embodiment, the mattress may have associated with it a heat exchanger, e.g. connected below the mattress or connected to the pump unit 10 or 98. In normal use, this heat exchanger may not function but may be connected into the air supply system to the mattress. Also, the pump unit may include a port which can opened to supply a separate air stream, e.g. to a cooling jacket. When cooling is required, a separate cooling unit can be supplied which has connections to the heat exchanger. The cooling unit may include a compressor, condenser and evaporator coil, together with a reservoir for water which is connectable to the heat exchanger.

In general, the source of coolant will be a refrigeration system operated using a compressor and a vaporizable refrigerant. However, other refrigerating systems can be employed such as thermoelectric coolers, which function by means of the Peltier effect. These have the advantage that they can easily be operated by a D. C. electrical supply.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. In any case, because the scope of the present invention is much broader than any particular embodiment, the foregoing detailed description should not be construed as a limitation of the scope of the present invention, which is limited only by the claims appended hereto.

What is claimed is:

1. A therapeutic combination for cooling a person's body while supporting the person in a supine position, said therapeutic combination comprising:

an inflatable mattress system for supporting a person in a supine position;

an inflatable cooling layer adapted to overlay the person while the person is supported upon said inflatable mattress system;

a source of pressurized fluid in communication with said inflatable mattress system and said inflatable cooling layer, said source being adapted to inflate said inflatable mattress system and to provide cooling fluid to said inflatable mattress system and said inflatable cooling layer; and said therapeutic combination being adapted to cool the person's core body temperature to a temperature of about 32 to 34° C.

2. The therapeutic combination as recited in claim 1, wherein said inflatable mattress system comprises a mattress overlay.

3. The therapeutic combination as recited in claim 1, wherein said inflatable cooling layer is adapted to cover at least the torso portion of the patient.

4. The therapeutic combination as recited in claim 3, wherein said inflatable cooling layer comprises a cooling jacket.

5. The therapeutic combination as recited in claim 4, wherein said cooling jacket comprises a plurality of apertures, said apertures being adapted to allow the passage of fluid from within to without said cooling jacket and thereby further cooling the patient's body.

6. The therapeutic combination as recited in claim 3, wherein said inflatable cooling layer comprises a cooling blanket.

7. The therapeutic combination as recited in claim 4, wherein said cooling blanket comprises a plurality of apertures, said apertures being adapted to allow the passage of fluid from within to without said cooling blanket and thereby further cooling the patient's body.

8. The therapeutic combination as recited in claim 1, wherein said inflatable mattress system comprises a plurality of compartments.

9. The therapeutic combination as recited in claim 8, wherein each said compartment is a sac in a low air loss mattress system.

10. The therapeutic combination as recited in claim 8, wherein each said compartment is separately inflatable.

11. The therapeutic combination as recited in claim 10, said therapeutic combination further comprising at least one valve interposed between said source of pressurized fluid and said inflatable mattress system.

12. The therapeutic combination as recited in claim 11, wherein said valve is adapted to control the inflation pressure of the fluid delivered from said source to said mattress system.

13. The therapeutic combination as recited in claim 12, wherein said valve is further adapted to control the temperature at the surface of said mattress system.

14. The therapeutic combination as recited in claim 13, said therapeutic combination further comprising a plurality of valves interposed between said source and said mattress system.

15. The therapeutic combination as recited in claim 14, wherein at least one said valve is interposed between said source and each said compartment.

16. The therapeutic combination as recited in claim 11, wherein said source of pressurized fluid is adapted to achieve a temperature of less than about 10° C. at the surface of said inflatable mattress system.

17. The therapeutic combination as recited in claim 1, said therapeutic combination further comprising:

a refrigeration circuit for producing a cooled media; and a heat exchanger, said heat exchanger being adapted to cool the fluid from said source of pressurized fluid by association with said cooled media produced by said refrigeration circuit.

18. The therapeutic combination as recited in claim 17, said therapeutic combination further comprising:

a temperature sensor associated with the surface of said inflatable mattress system for measuring the surface temperature of said mattress system; and a controller associated with said heat exchanger and said temperature sensor, said controller being adapted to adjust the temperature of the pressurized fluid passed through said heat exchanger in response to the temperature measured at the surface of said mattress system.

19. The therapeutic combination as recited in claim 18, wherein said temperature sensor comprises a thermistor positioned at an outlet from said heat exchanger.

20. The therapeutic combination as recited in claim 1, said therapeutic combination further comprising a confining system adapted to restrain the person on said inflatable mattress system during the provision of cooling therapy.

21. A therapeutic combination for cooling a person's body while supporting the person in a supine position, said therapeutic combination comprising:

an inflatable mattress system for supporting a person in a supine position;

a layer adapted to overlay and form an enclosure over the person while the person is supported upon said inflatable mattress system;

a source of pressurized fluid in communication with said inflatable mattress system, said source being adapted to inflate said inflatable mattress system and to provide cooling fluid to said inflatable mattress system and said enclosure; and said therapeutic combination being adapted to cool the person's core body temperature to a temperature of about 32 to 34° C.

22. A therapeutic combination for cooling a person's body while supporting the person in a supine position, said therapeutic combination comprising:

an inflatable mattress system for supporting a person in a supine position;

an inflatable cooling layer adapted to overlay the person while the person is supported upon said inflatable-mattress system;

a source of pressurized and refrigerated air in communication with said inflatable mattress system and said inflatable cooling layer, said source being adapted to inflate said inflatable mattress system and to provide a flow of refrigerated air through said inflatable mattress system and through said inflatable cooling layer; and whereby said therapeutic combination is adapted to cool the person's core body temperature to a temperature of about 32 to 34° C.

23. The therapeutic combination as recited in claim 22, wherein said refrigerated air is cooled to a temperature of less than about 3° C.

* * * * *